(12) United States Patent
Einck et al.

(10) Patent No.: US 11,806,163 B2
(45) Date of Patent: Nov. 7, 2023

(54) HYDRATION TESTING ARTICLE

(71) Applicant: Cydney Einck, Edina, MN (US)

(72) Inventors: Cydney Einck, Edina, MN (US); David Gilbert Sime, Minnetonka, MN (US); James B. Priebnow, Coon Rapids, MN (US)

(73) Assignee: Inter.mix, Inc., Brooklyn Center, MN (US)

( * ) Notice: Subject to any disclaimer, the term of this patent is extended or adjusted under 35 U.S.C. 154(b) by 902 days.

(21) Appl. No.: 16/597,058

(22) Filed: Oct. 9, 2019

(65) Prior Publication Data
US 2020/0178893 A1  Jun. 11, 2020

Related U.S. Application Data

(60) Provisional application No. 62/743,121, filed on Oct. 9, 2018.

(51) Int. Cl.
*A61B 5/00* (2006.01)
*A61B 5/145* (2006.01)

(52) U.S. Cl.
CPC ........ *A61B 5/4875* (2013.01); *A61B 5/14517* (2013.01); *A61B 2503/10* (2013.01); *A61B 2503/20* (2013.01); *A61B 2562/0295* (2013.01)

(58) Field of Classification Search
CPC .............. A61B 5/4875; A61B 5/14517; A61B 2503/10; A61B 2503/20
See application file for complete search history.

(56) References Cited

U.S. PATENT DOCUMENTS

| 3,552,929 A | 1/1971 | Fields et al. |
| 4,457,748 A | 7/1984 | Lattin et al. |

(Continued)

FOREIGN PATENT DOCUMENTS

| WO | 9414062 | 6/1994 |
| WO | 0191853 | 12/2001 |

(Continued)

OTHER PUBLICATIONS

Baker, Lindsay B. et al., "Sweat Testing Methodology in the Field: Challenges and Best PracticesSweat Testing," Sports Science Exchange (2016) vol. 28, No. 161 (6 pages).

(Continued)

*Primary Examiner* — Jacqueline Cheng
*Assistant Examiner* — Tho Q Tran
(74) *Attorney, Agent, or Firm* — Pauly, DeVries Smith & Deffner LLC

(57) ABSTRACT

Embodiments herein include testing articles to assess hydration of a test subject. The testing articles can include a carrier portion having a porous medium through which a fluid of the test subject moves. The carrier portion can include a first end and a second end opposite the first end. The testing articles can include a first chemical composition disposed in the porous medium that reacts with chloride ions to produce a first color change. The testing articles can include a wick that is in direct contact with the first end of the carrier portion to allow the transfer of the fluid from the wick to the carrier portion. The testing articles can include a fill indicator element in direct contact with the second end of the carrier portion to allow the transfer of the fluid from the carrier portion to the fill indicator element. Other embodiments are also included herein.

21 Claims, 11 Drawing Sheets

(56) References Cited

U.S. PATENT DOCUMENTS

| | | | |
|---|---|---|---|
| 4,756,314 A | 7/1988 | Eckenhoff et al. | |
| 4,846,182 A * | 7/1989 | Fogt | G01N 33/84 600/362 |
| D326,716 S | 6/1992 | Mortara | |
| 5,125,405 A | 6/1992 | Schmid et al. | |
| D336,444 S | 6/1993 | Anderson et al. | |
| 5,312,326 A | 5/1994 | Myers et al. | |
| 5,438,984 A | 8/1995 | Schoendorfer | |
| 5,465,713 A | 11/1995 | Schoendorfer | |
| D371,605 S | 7/1996 | Wong et al. | |
| 5,624,415 A * | 4/1997 | Cormier | A61N 1/0432 604/20 |
| 5,800,685 A | 9/1998 | Perrault | |
| 5,817,012 A | 10/1998 | Schoendorfer | |
| 6,042,543 A * | 3/2000 | Warwick | A61B 5/4266 600/362 |
| D425,203 S | 5/2000 | Sheehan et al. | |
| D443,063 S | 5/2001 | Pisani | |
| D452,564 S | 12/2001 | Micinski et al. | |
| 6,347,246 B1 | 2/2002 | Perrault et al. | |
| D467,349 S | 12/2002 | Niedbala et al. | |
| D479,879 S | 9/2003 | Dickinson | |
| 6,745,071 B1 | 6/2004 | Anderson et al. | |
| D495,055 S | 8/2004 | Silber | |
| D541,421 S | 4/2007 | Metzger et al. | |
| 7,206,630 B1 | 4/2007 | Tarler et al. | |
| 7,286,865 B2 | 10/2007 | Nazeri | |
| D557,809 S | 12/2007 | Neverov et al. | |
| D598,114 S | 8/2009 | Cryan | |
| D603,051 S | 10/2009 | Causevic et al. | |
| D625,823 S | 10/2010 | Schneider et al. | |
| D647,209 S | 10/2011 | Mueller et al. | |
| D658,299 S | 4/2012 | Mcgusty et al. | |
| D658,768 S | 5/2012 | Parker, Iii et al. | |
| 8,180,425 B2 | 5/2012 | Selvitelli et al. | |
| D663,431 S | 7/2012 | Parker, Iii et al. | |
| D663,849 S | 7/2012 | Mcgusty et al. | |
| D665,501 S | 8/2012 | Shibata et al. | |
| D665,917 S | 8/2012 | Termaat et al. | |
| 8,238,996 B2 | 8/2012 | Burnes et al. | |
| D669,186 S | 10/2012 | Gozani | |
| D669,187 S | 10/2012 | Gozani | |
| 8,298,484 B2 | 10/2012 | Takagi et al. | |
| D674,096 S | 1/2013 | Gaw et al. | |
| D681,231 S | 4/2013 | Steinhauer et al. | |
| 8,734,341 B2 * | 5/2014 | Howell | A61B 5/4875 424/9.1 |
| D717,960 S | 11/2014 | Einck et al. | |
| 9,883,827 B2 | 2/2018 | Nyberg et al. | |
| 2002/0099277 A1 | 7/2002 | Harry et al. | |
| 2003/0055477 A1 | 3/2003 | Dupelle et al. | |
| 2005/0215918 A1 | 9/2005 | Frantz et al. | |
| 2008/0177168 A1 | 7/2008 | Callahan et al. | |
| 2010/0318018 A1 | 12/2010 | Schonenberger et al. | |
| 2011/0077497 A1 | 3/2011 | Oster et al. | |
| 2012/0042722 A1 * | 2/2012 | Song | G01N 33/558 73/32 R |
| 2012/0046628 A1 * | 2/2012 | Wei | G01N 21/81 604/361 |
| 2012/0143159 A1 * | 6/2012 | Wei | A61F 13/84 604/361 |
| 2014/0100436 A1 | 4/2014 | Brunner et al. | |
| 2014/0135679 A1 | 5/2014 | Mann et al. | |
| 2014/0257064 A1 | 9/2014 | Einck et al. | |
| 2015/0141775 A1 * | 5/2015 | Macaluso | A61B 10/0064 600/307 |
| 2015/0216471 A1 * | 8/2015 | Goldstein | A61B 5/682 600/573 |
| 2016/0135741 A1 * | 5/2016 | Chetham | A61B 5/08 600/391 |
| 2017/0231571 A1 * | 8/2017 | Rogers | A61B 5/1455 600/301 |
| 2017/0296114 A1 * | 10/2017 | Ghaffari | A61B 5/4266 |
| 2018/0042585 A1 * | 2/2018 | Heikenfeld | G01N 33/48792 |
| 2020/0129112 A1 * | 4/2020 | Model | A61B 5/4266 |

FOREIGN PATENT DOCUMENTS

| | | |
|---|---|---|
| WO | 2005018443 | 3/2005 |
| WO | 2008146224 | 12/2008 |
| WO | 2009134826 | 11/2009 |
| WO | 2014164842 | 10/2014 |

OTHER PUBLICATIONS

Choi, Jungil et al., "Skin-Interfaced Systems for Sweat Collection and Analytics," Science Advances, Feb. 16, 2018 (10 pages).

Curto, Vincenzo F. et al., "Real-Time Sweat pH Monitoring Based on a Wearable Chemical Barcode Micro-fluidic Platform Incorporating Ionic Liquids," Sensors and Actuators B: Chemical, vols. 171-172, Aug.-Sep. 2012, pp. 1327-1334 (8 pages).

File History for U.S. Appl. No. 14/204,842 retrieved Jan. 2, 2020 (273 pages).

Goncalves, Aline C. et al., "Chloride and Sodium Ion Concentrations in Saliva and Sweat as a Method to Diagnose Cystic Fibrosis," J Pediatr (Rio J). 2019;95(4):443-450 (8 pages).

Heikenfeld, J. et al., "Wearable Sensors: Modalities, Challenges, and Prospects," Lab on a Chip, The Royal Society of Chemistry; 2018, 18, 217-248 (33 pages).

Herrmann, Franz et al., "Studies of pH of Sweat Produced By Different Forms of Stimulation," Journal of Investigative Dermatology, vol. 24, Issue 3 pp. 141-373 (Mar. 1955), 22 pages.

Jadoon, Saima et al., "Recent Developments in Sweat Analysis and Its Applications," International Journal of Analytical Chemistry, vol. 2015, Article ID 164974, 7 pages, 2015 (7 pages).

Kenefick, Robert W. et al., "Chapter 70: Dehydration and Rehydation," Wilderness Medicine Textbook 2012 (16 pages).

Kim, Sung B. et al., "Super-Absorbent Polymer Valves and Colorimetric Chemistries for Time-Sequenced Discrete Sampling and Chloride Analysis of Sweat via Skin-Mounted Soft Microfluidics," Small Journal 2018 (11 pages).

Ladell, W. S. S. "The Changes in Water and Chloride Distribution During Heavy SweatingThe Changes in Water," J. Physiol. (1949) 108, 440-450 (1 pages).

Lewis, D. et al., "Considering Exercise-Associated Hyponatraemia as a Continuum," BMJ Case Rep., Mar. 9, 2018 (1 page), abstract only.

Morris, Amanda "New Microfluidic Devices Help Athletes and Enhance Physical Rehab," Northwestern University, Feb. 16, 2018 <https://news.northwestern.edu/stories/2018/february/new-microfluidic-devices-help-athletes-and-enhance-physical-rehab/> (4 pages).

Mu, Xuan et al., "A Paper-Based Skin Patch for the Diagnostic Screening of Cystic Fibrosis," Chem. Commun., 2015, 51, 6365-6368 (4 pages).

Patterson, Mark J. et al., "Variations in Regional Sweat Composition in Normal Human Males," Exp Physiol. Nov. 2000;85(6):869-75 (8 pages).

Raj, Goutham et al., "Wireless Sweat Signal Analyser," American Journal of Computer Science and Information Technology, available as early as Aug. 23, 2017 (http://www.imedpub.com/abstract/wireless-sweat-signal-analyser-17165.html), 3 pages.

Venere, Emil et al., "Low-cost paper-based skin patch monitors dehydration by changing color from sweat," Purdue University News, Dec. 6, 2016, <https://www.purdue.edu/newsroom/releases/2016/Q4/low-cost-paper-based-skin-patch-monitors-dehydration-by-changing-color-from-sweat.html> (4 pages).

Warwick, Warren J. et al., "Quantification of Chloride in Sweat wit the Cystic Fibrosis Indicator System," Clin. Chem. 36/1, 96-98 (1990), 3 pages.

* cited by examiner

HYDRATION TESTING ARTICLE

This application claims the benefit of U.S. Provisional Application No. 62/743,121, filed Oct. 9, 2018, the content of which is herein incorporated by reference in its entirety.

FIELD

Embodiments herein relate to hydration testing articles. More specifically, the embodiments herein relate to hydration testing articles that include a carrier portion that undergoes a colorimetric change upon binding of an analyte in a fluid of a test subject.

BACKGROUND

The hydration state of an individual is of great interest to athletes, military personnel, medical professionals, laborers, and more. Testing the sweat of an individual for various analytes can provide information as to the hydration state of the individual.

However, gathering a body fluid sample of an individual in real time using techniques such as venipuncture, urine or saliva collection, or other invasive or semi-invasive means is not always practical, such as when a marathon runner is in the middle of a race, when a member of the military is deployed in the field, or when a construction worker is hard at work on a job site. Likewise, direct sampling through collection and removal of a sweat sample is time consuming and difficult to execute in the field.

SUMMARY

Embodiments herein include a testing article to assess hydration of a test subject. The testing article can include a carrier portion having a porous medium through which a fluid of the test subject moves. The carrier portion can have a first end and a second end opposite the first end, where the fluid of the test subject enters the carrier portion at or near the first end. The testing article can include a first chemical composition disposed in the porous medium, where the chemical composition reacts with chloride ions to produce a first color change. The testing article can include a wick, where the wick is in direct contact with the first end of the carrier portion to allow the transfer of the fluid from the wick to the carrier portion. The testing article can include a fill indicator element in direct contact with the second end of the carrier portion to allow the transfer of the fluid from the carrier portion to the fill indicator element.

In an embodiment, the testing article includes a second chemical composition that reacts with the fluid of the test subject to produce a second color change, where the second color change is different than the first color change and where the second chemical composition is disposed in the porous medium of the carrier portion.

In an embodiment, the testing article includes a second chemical composition configured to migrate along with the fluid of the test subject through the porous medium of the carrier portion and into the fill indicator element.

In an embodiment, the testing article includes a fill indicator element having a second chemical composition that reacts with the fluid of the test subject to produce a second color change, where the second color change is different than the first color change.

In an embodiment, the testing article includes a testing article having a wick that lacks the first chemical composition.

In an embodiment, the testing article includes a wick that is attached to the carrier portion by virtue of a joint selected from the group included a butt joint, an overlapping joint, or any other joint that provides sufficient continuity of flow from the wick to the carrier portion.

In an embodiment, the testing article includes a wick that is integrally formed with the carrier portion.

In an embodiment, the testing article includes a wick that includes a porous medium.

In an embodiment, the testing article includes a wick with a porous medium that is the same as the porous medium of the carrier portion.

In an embodiment, the testing article includes a wick with a porous medium that is different than the porous medium of the carrier portion.

In an embodiment, the testing article includes a porous medium of the wick that exhibits greater wicking efficiency than the porous medium of the carrier portion.

In an embodiment, the testing article includes a testing article that can include an activation tab disposed under the wick, the activation tab configured to be removed to expose the wick at a later time point.

In an embodiment, the testing article includes a porous medium of the carrier portion can include a fibrous mat.

In an embodiment, the testing article includes a first chemical composition including silver chromate.

In an embodiment, the testing article includes a second chemical composition including at least one of phenol red, methyl orange, brilliant yellow, bromocresol green, malachite green, bromophenol blue, or bromocresol purple.

In an embodiment, the testing article includes a cross-sectional area of the carrier portion that varies along its length between the first end and the second end.

In an embodiment, the testing article includes the average cross-sectional area of the carrier portion at the first end is greater than at the second end.

In an embodiment, the testing article includes the average cross-sectional area of the carrier portion at the second end is greater than at the first end.

In an embodiment, the testing article includes the carrier portion that includes two lateral edges, the lateral edges defining a scalloped shape.

In an embodiment, the testing article includes a carrier portion that includes a linear strip.

In an embodiment, the testing article includes a carrier portion that includes a circular shape.

In an embodiment, the testing article includes a carrier portion that includes an ovoid shape.

In an embodiment, the testing article includes a carrier portion that includes a trapezoidal shape.

In an embodiment, the testing article includes a carrier portion that includes a triangular shape.

In an embodiment, the testing article includes a support substrate providing structural support to the carrier portion In an embodiment, the testing article includes a support substrate that is disposed under the carrier portion.

In an embodiment, the testing article includes a support substrate that is disposed under at least a portion of the wick.

In an embodiment, the testing article includes a moisture vapor barrier layer.

In an embodiment, the testing article includes a moisture vapor barrier layer that encapsulates at least one of the carrier portion, the fill indicator element, or a portion of the wick.

In an embodiment, the testing article includes a first moisture vapor barrier layer disposed over the carrier portion and a second moisture vapor barrier layer disposed under the carrier portion.

In an embodiment, the testing article includes a first moisture vapor barrier layer that is opaque.

In an embodiment, the testing article includes a first moisture vapor barrier layer that defines one or more transparent windows.

In an embodiment, an opaque hydrochromic ink is included that optically obscures at least one of the transparent windows.

In an embodiment, the first chemical composition further comprising a buffer having a pH of between 5.46 and 7.5

In an embodiment, the carrier portion includes a curved portion dividing an upper portion and a lower portion, wherein the upper portion is disposed on top of one another.

In an embodiment, a first release-liner disposed over a top surface of the upper portion and a second release-liner disposed under a lower surface of the lower portion.

In an embodiment, the invention includes a testing article to assess hydration of a test subject. The testing article can include a carrier portion including a porous medium through which a fluid of the test subject moves. The carrier portion includes a first end and a second end opposite the first end, where the fluid of the test subject enters the carrier portion essentially at or near the first end. The carrier portion includes a first chemical composition disposed in the porous medium, where the chemical composition reacts with chloride ions to produce a first color change. The testing article includes a wick, where the wick is in direct contact with the first end of the carrier portion to allow the transfer of the fluid from the wick to the carrier portion.

In an embodiment, the testing article includes a fill indicator element in direct contact with the second end of the carrier portion to allow the transfer of fluid from the carrier portion to the fill indicator element.

In an embodiment, the testing article includes an absorbent layer including a second chemical composition that reacts with the fluid of a test subject to produce a second color change, where the second color change is different than the first color change.

In an embodiment, the testing article includes a fill indicator element including a second chemical composition that reacts with the fluid of a test subject to produce a second color change, where the second color change is different than the first color change This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Monitoring the hydration state of an individual is of great interest to many, including athletes, military personnel, medical professionals, laborers, etc. In accordance with various embodiments herein, a testing article for assessing the hydration state of a test subject is provided. The testing article can be worn by a test subject (or otherwise put in contact with) during an athletic endeavor, while deployed in the field of a military mission, while working in hot and strenuous work environments, while a patient in a hospital or managed care setting, or at any time hydration state is of interest.

The testing articles described herein can provide a real-time visual indication of a hydration state based on a colorimetric change indicative of, or associated with, some change in the physical or chemical makeup of one or more of the components of the testing article. In some embodiments the testing article can be calibrated to allow quantitative estimates to be derived from the visual indications. In various embodiments herein, the testing article can provide a rapid, direct and real-time indication of a hydration state of a subject.

In some embodiments, a visual change can include a reaction between chloride ions present in the sweat of a test subject and silver chromate present in the testing article. When silver chromate (typically a rust color) immobilized on a substrate reacts with chloride ions in sweat, a white silver chloride precipitate forms that can be easily visualized by the human eye, such as a leading edge of a precipitation front.

The adequacy or completeness of the penetration of the fluid being sampled into the testing article can be determined using a fill indicator element. In various embodiments, a chemical indicator can be present in the testing article outside of the fill indicator element when in a starting state. As fluid passes through the testing article and ultimately into the fill indicator element, it can carry the chemical indicator with it causing a color change in the fill indicator element so that the user knows that a sufficient sample volume of fluid has entered the testing article. In other embodiments, the chemical indicator can be present in the fill indicator element itself.

Various chemical indicators can be used for purposes of the fill indicator element functionality, including, but not limited to, the colorimetric indicators phenol red, methyl orange, brilliant yellow, bromocresol green, malachite green, bromophenol blue, or bromocresol purple, etc.

Figure 1:
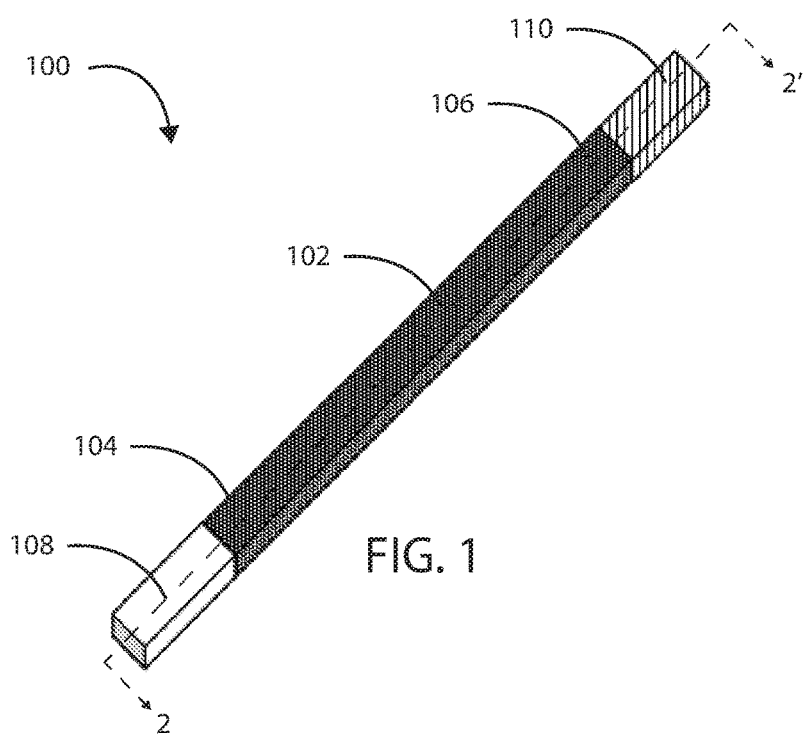
FIG. 1 is a schematic perspective view of components of a testing article in accordance with various embodiments herein.
Figure 2:
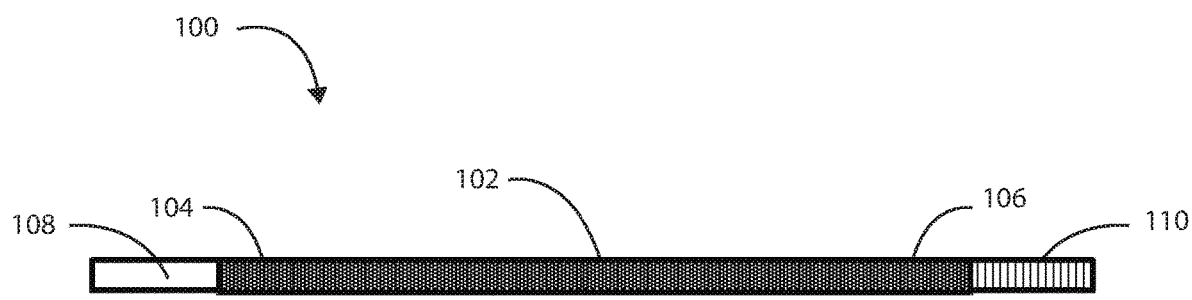
FIG. 2 is a schematic cross-sectional view of components of a testing article shown in FIG. 1 along line 2-2' in accordance with various embodiments herein.

Referring now to FIG. 1, a perspective view of a testing article 100 is shown in accordance with the embodiments herein. FIG. 2 shows a cross-sectional view of the testing article 100 of FIG. 1 along line 2-2'. The testing article 100 shown in FIGS. 1 and 2 can include a carrier portion 102, a wick 108, and a fill indicator element 110.

The carrier portion 102 can include a porous medium through which a fluid of a test subject can move via capillary action and/or other mechanisms. In some embodiments, the porous medium of the carrier portion 102 can include a fibrous mat, a woven material, or an electrospun material. In some embodiments, the carrier portion 102 can be formed from a hydrophilic polymer. In some embodiments, the carrier portion 102 can be formed from a polyester, a polyamide (NYLON), or an acrylic. In some embodiments, the carrier portion can be formed from a cellulosic material. In some embodiments, the carrier portion can be formed from methylcellulose or nitrocellulose. In various embodiments, the carrier portion can specifically be formed using a strip of absorbent paper such as GE WHATMAN™ CR-20 chromatography paper or any other sufficiently absorbent paper onto which the test chemistry for the test is applied for absorption. In some embodiments the carrier portion can be substantially non-absorbent. In some embodiments the carrier portion can be formed of a material such as a non-absorbent membrane. In some embodiments the carrier portion can be formed of a material such as a microfiltration membrane. In some embodiments the carrier portion can be formed of a material such as a mixed cellulose ester.

In some embodiments, the fluid of the test subject is sweat.

The carrier portion 102 of testing article 100 can include a first end 104 and a second end 106 opposite the first end 104. The fluid of the test subject can enter the carrier portion at the first end 104. The carrier portion 102 can include a test chemistry including a first chemical composition disposed on the surface of or within the porous medium. In some embodiments, the first chemical composition can be disposed on the surface of a non-porous or semi-porous substrate. The first chemical composition can react with chloride ions in the fluid of the test subject to produce a first color change in the carrier portion 102. In some embodiments, the first chemical composition can include silver chromate. In some embodiments, the first chemical composition can include silver nitrate. In some embodiments, the first chemical composition can include potassium chromate. In some embodiments, the first chemical composition can include silver nitrate and potassium chromate, which can react to form silver chromate ($K_2CrO_4 + 2AgNO_3 \rightleftharpoons Ag_2CrO_4 + 2KNO_3$). As discussed above, when silver chromate (typically a rust color) immobilized on a substrate reacts with chloride ions in sweat, a white silver chloride precipitate forms that can be easily visualized by the human eye, such as a leading edge of a precipitation front.

In some embodiments, the carrier portion can include a second chemical composition that can further include a chemical indicator. The second chemical composition can react with the fluid of the test subject to produce a second color change, where the second color change is different than the first color change. The second chemical composition can be disposed in the porous medium of the carrier portion, including disposed along with the first chemical composition or disposed separately. The second chemical composition can migrate along with the fluid of the test subject through the porous medium of the carrier portion and into the fill indicator element.

The test chemistry applied in the case of a chloride detection testing article, can be a compound of silver chromate (See Warwick, 2000, U.S. Pat. No. 6,042,543, which is incorporated herein by reference) formed in situ by the successive application of silver nitrate and potassium chromate. The absolute and relative solution strengths of the test chemistry materials can be used to alter the sensitivity and the speed of the tests to be made with the testing article.

The uniform absorption of the test chemistry applied onto the carrier portion can be aided, or modified, by the use of one or more buffer solutions, wherein the buffer solution can include one or more of phosphate compounds, citrate compounds, acetate compounds, Tris (tris(hydroxymethyl)aminomethane), or the like, or blends of any of the foregoing. The specific compounds and ratios of same in the buffer solution can both alter the resulting pH of the test chemistry and influence the uniformity of absorption by the carrier portion. In some embodiments, the buffer solution can have a pH of between 5.46 and 7.5. In some embodiments, the buffer solution can have a pH of about 5.46, 5.6, 5.8, 6.0, 6.2, 6.4, 6.6, 6.8, 7.0, 7.2, 7.4 or 7.5, or can have a pH falling within a range between any of the foregoing.

Various techniques can be used for application of the test chemistry to the carrier portion, including, but not limited to, any of direct immersion of the strip, soaking or spraying onto the strip, or any of a large number of direct or indirect selective deposition techniques.

In various embodiments, the testing article 100 can include a wick 108. The wick 108 can be in direct contact with the first end 104 of the carrier portion 102 to allow the transfer of the fluid of the test subject from the wick 108 to the carrier portion 102. In some embodiments, the wick 108 can be attached to the first end 104 of the carrier portion 102 by virtue of a joint selected from the group including a butt joint, an overlapping joint, or another means of providing continuity between the two parts such as an adhesive, a bridge, a connector, or the like. By way of example, the wick 108 shown in FIG. 1 is attached to the first end 104 of the carrier portion 102 by a butt joint. In other embodiments, the wick 108 can be integrally formed with the carrier portion 102. In some embodiments, the joint can include any joint that provides sufficient continuity of flow from the wick to the carrier portion. In some embodiments, the wick 108 does not include the first chemical composition like that disposed in the porous medium of the carrier portion 102.

It will be appreciated that in some embodiments the wick 108 can be made from a porous medium through which a fluid of a test subject can move via capillary action. In some embodiments, the fluid of a test subject can move through the wick by other types of fluid flow, such as steady flow, unsteady flow, compressible flow, incompressible flow, and the like. In some embodiments, the wick 108 can be made from the same porous medium as the carrier portion 102 or from a different porous medium than the carrier portion 102. In some embodiments, the porous medium of the wick 108 can exhibit greater wicking efficiency than the porous medium of the carrier portion 102. In some embodiments, the wick material can include a fibrous mat, a woven material, or an electrospun material. In some embodiments, the wick material can be formed from a hydrophilic polymer. In some embodiments, the wick material can be made from a polyester, a polyamide (NYLON), an acrylic, or other hydrophilic polymer material. In some embodiments, the wick material can be formed from a cellulosic material. In some embodiments, the wick material can be formed from methylcellulose or nitrocellulose.

It will be appreciated that in some embodiments, the wick can be formed from the same material as the carrier portion such that the wick is continuous with the carrier portion. In embodiments where the wick is continuous with the carrier portion, the wick can be formed by various methods, including but not limited to using embossing techniques to inhibit any potential backward flow of the test chemistry from the testing article to the test subject. In other embodiments, the wick can be formed from a different material than the carrier portion, such as a material designed to act more effectively as a wick like Grade 934-AH® microfiber filters. In embodiments where the wick is formed from a material different than the carrier portion, the wick material can be configured to be devoid of the test chemistry and thus can form a physical barrier separating the test chemistry from the test subject. By way of example, the wick can be used to provide mechanical and chemical separation between the test subject and the test chemistry of the carrier portion. This can be important when the test chemistry used to detect the analytes to be measured is not compatible with intimate contact with the surface (e.g., skin) of the test subject. In such embodiments, the wick would not include the test chemistry, and would simply allow the passage of the sweat from the subject.

However, it will be appreciated that in various embodiments herein a wick is not included. In some embodiments, other components of the testing article 100 (such as the carrier portion) can be configured to be in direct contact with a test subject's skin (or other source of fluid for testing). In some embodiments, an aperture in a material layer (such as a support substrate or other component) allows access of the fluid to other components of the testing article 100.

The testing article 100 can include a fill indicator element 110. The fill indicator element 110 can be in direct contact with the second end 106 of the carrier portion 102 to allow the transfer of fluid from the carrier portion 102 to the fill indicator element 110. In some embodiments, the fill indicator element 110 can be attached to the second end 106 of the carrier portion 102 by virtue of a joint selected from the group including a butt joint or an overlapping joint. By way of example, the fill indication element shown in FIG. 1 is attached to the second end 106 of the carrier portion 102 by a butt joint. In other embodiments, the fill indicator element 110 can be integrally formed with the carrier portion 102. In some embodiments, the joint can include any joint that provides sufficient continuity of flow from the carrier portion to the fill indicator element.

The fill indicator element 110 can include a second chemical composition that reacts with a fluid to produce a second color change, where the second color change is different than the first color change observed within the carrier portion 102 due to a change in the first chemical composition. In some embodiments the second chemical composition can include a chemical indicator. In some embodiments, the fill indicator element can be devoid of a first or second chemical composition, and rather, a second chemical composition can be included in the carrier portion and can be transported into the fill indicator element when the fluid of a subject is wicked along the testing element. The second chemical composition can include at least one chemical indicator selected from the group including the colorimetric indicators phenol red, methyl orange, brilliant yellow, bromocresol green, malachite green, bromophenol blue, bromocresol purple, etc.

It will be appreciated that in some embodiments the fill indicator element 110 can be made from a porous medium. The fill indicator element 110 can be made from the same porous medium as the carrier portion 102 or from a different porous medium than the carrier portion 102. In some embodiments, the porous medium of the fill indicator element 110 can exhibit the same, lesser, or greater wicking efficiency than the porous medium of the carrier portion 102. In some embodiments, the fill indicator element can be made from one or more hydrophilic polymers. In various embodiments, the fill indicator element can be formed from the same material as the carrier portion such that the fill indicator element is continuous with the carrier portion. In other embodiments, the fill indicator element can be formed from a different material than the carrier portion. In embodiments where the fill indicator element is a continuous part of the carrier portion, the fill indicator element can be formed by various methods, including but not limited to using embossing techniques to inhibit any potential backward flow of the test chemistry within the testing article.

It will be appreciated that the fill indicator element can be made either as a continuous part of the carrier portion or as an attached component using a different substrate. The requirement is that the fluid transfer from the carrier portion to the fill indicator element be predictable, reliable, and sufficiently rapid as not to inhibit the purpose of showing the sufficiency of the test sample. In some embodiments, an approach can include physically attaching a piece of moisture detection paper, such as those containing Cobalt compounds, such as is commercially available, (e.g., Indigo Instrument's Cobalt Chloride test strips) or other material creating a visibly noticeable change upon contact with water.

In some embodiments, more than one fill indicator element can be attached, integrated, or otherwise connected to the testing article at intermediate points between the first end 104 and second end 106 of testing article 100 in order to provide indication of the progress of the fluid of the test subject as it travels along and through the carrier portion 102 of testing article 100 before the complete sample is collected. In some embodiments, multiple fill indicator elements can be present along testing article 100 to show progression of a fluid of a test subject through the testing article 100.

Figure 3:
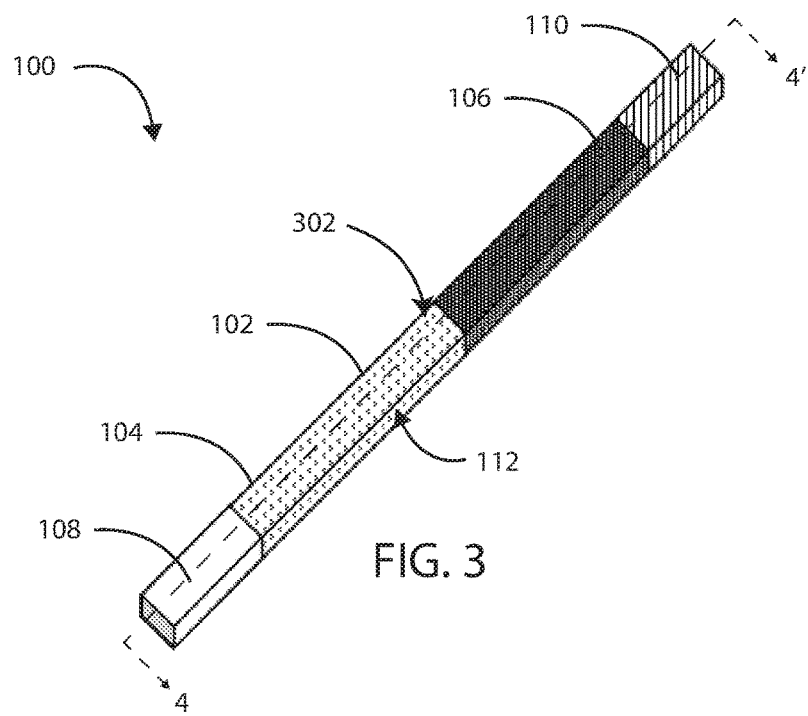
FIG. 3 is a schematic perspective view of components of a testing article in accordance with various embodiments herein.
Figure 4:
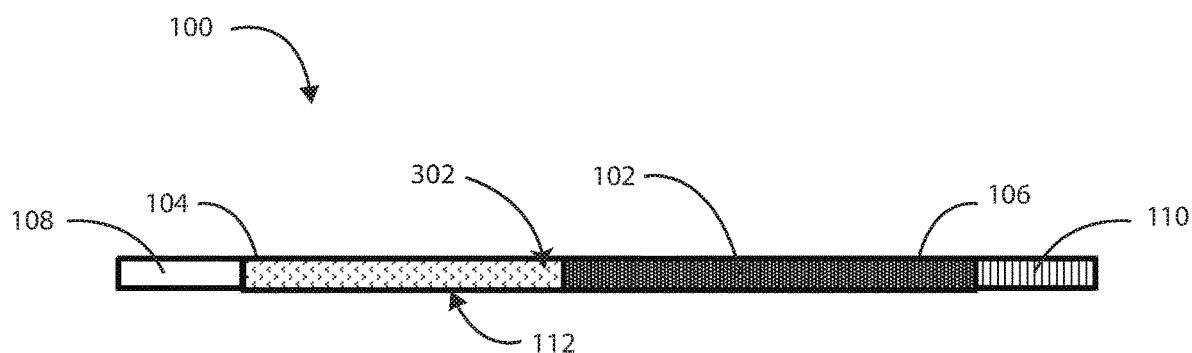
FIG. 4 is a schematic cross-sectional view of components of a testing article shown in FIG. 3 along line 4-4' in accordance with various embodiments herein.

After filling with sweat (which can be indicated by color change within one or more the fill indicator elements 110), the testing article 100 can be visually inspected by a subject, other individual or device to observe the first color change within the carrier portion 102. By way of example, referring now to FIG. 3, a perspective view of a testing article 100 is shown in accordance with the embodiments herein. FIG. 4 shows a cross-sectional view of the testing article 100 of FIG. 3 along line 4-4'. The testing article 100 shown in FIGS. 3 and 4 includes a first chemical composition disposed in the porous medium that has at least partially reacted with chloride ions in the fluid of the test subject to produce a first color change 112 in the carrier portion 102, as indicated by the disappearance of color from the carrier portion 102. It will be appreciated that once the fluid from the carrier portion 102 reaches the fill indicator element 110, a second color change, different than the first color change 112, can be observed (not shown) within the fill indicator element 110.

When fluid reaches the fill indicator element 110, the location of the leading edge 302 of the first color change 112 is indicative of the degree of hydration of the individual. The closer the leading edge 302 is to where fluid enters (such as by the wick near first end 104 of the carrier portion 102) the lower the concentration of chloride ions in the sweat and therefore the more hydrated the individual is. The closer the leading edge 302 is towards the fill indicator element 110 near second end 106 of the carrier portion 102, the higher the concentration of chloride ions in the sweat and therefore the less hydrated (i.e., the more dehydrated) the individual is.

Figure 5:
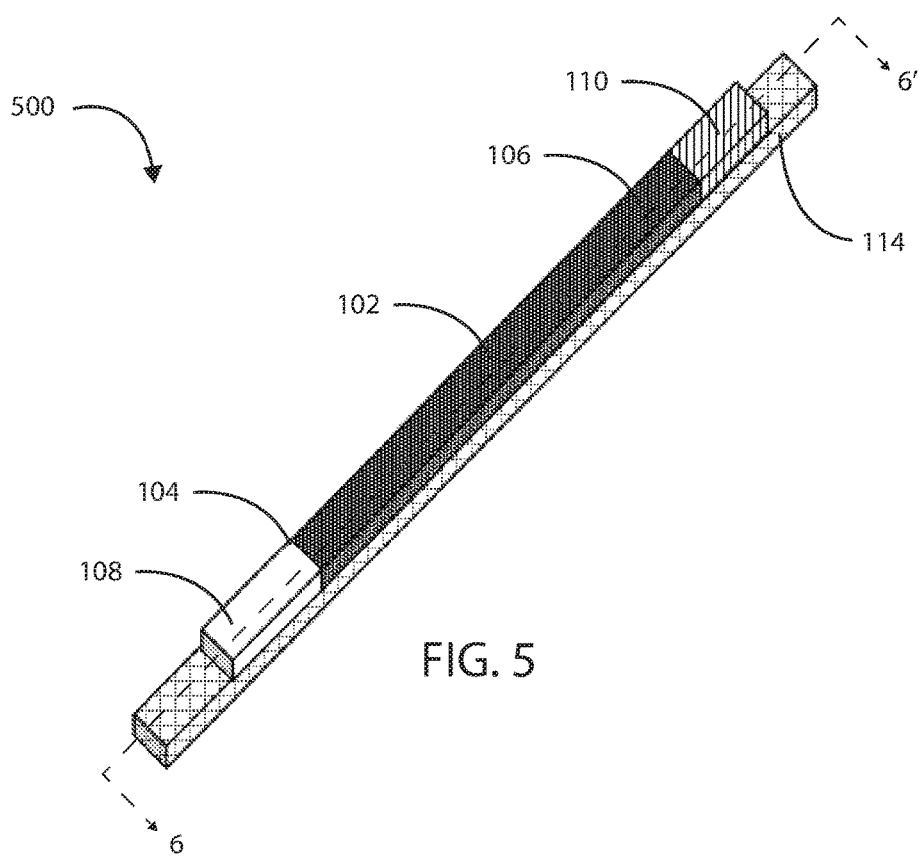
FIG. 5 is a schematic perspective view of components of a testing article in accordance with various embodiments herein.
Figure 6:
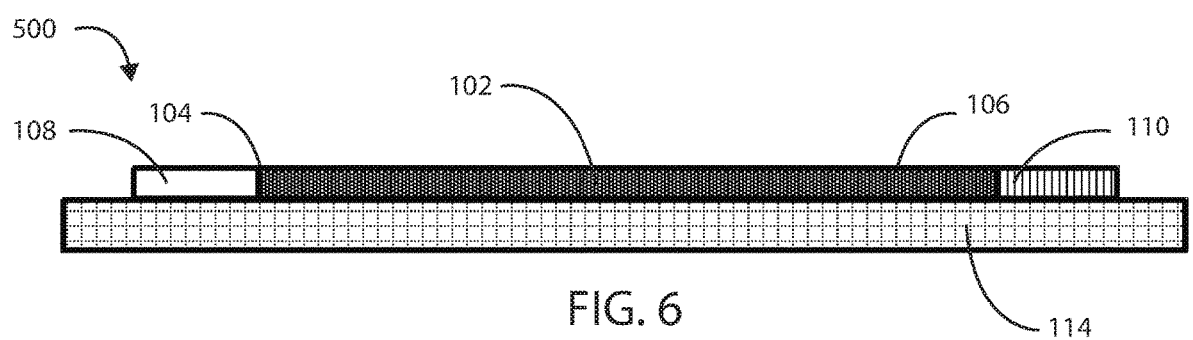
FIG. 6 is a schematic cross-sectional view of components of a testing article shown in FIG. 5 along line 6-6' in accordance with various embodiments herein.

In some embodiments, the testing articles embodied herein can include various other features. By way of example, the testing articles can include a support substrate to provide structural support to the testing article. Referring now to FIG. 5, a perspective view of a testing article 500 is shown in accordance with the embodiments herein. FIG. 6 shows a cross-sectional view of the testing article 500 of FIG. 5 along line 6-6'. The testing article 500 shown in FIGS. 5 and 6 includes the features common to those discussed above with respect to testing article 100 depicted in FIGS. 1-4.

Testing article 500 includes a support substrate 114 to provide structural support to the carrier portion 102, to the wick 108, and/or to the fill indicator element 110. In some embodiments, the support substrate 114 can extend the entire width of the short axis of the testing article 500, as shown, while in other embodiments, the support substrate 114 can extend a partial width of the short axis of the testing article 500 to leave the wick partially exposed on at least one lateral side of the support substrate 114. The support substrate can be made of various materials. The materials can be translucent, semi-translucent, or opaque. In some embodiments, the support substrate can be made from a polymer, such as a water impermeable polymer. In some embodiments, the support substrate can be a material (such as a polymer solution) sprayed onto the carrier portion 102 that later cures or otherwise strengthens sufficiently to provide the mechanical support needed, and thus may not exist as a distinct or completely distinct layer separate from the carrier portion 102. In some embodiments the support substrate can exist as a laminate with the carrier portion 102. Some embodiments can be more rigid and some embodiments can be flexible as required for the particular field and location of use.

The support substrate 114 can provide structural support to one or more regions of the testing article. In some embodiments, the support substrate 114 can support the entirety of the carrier portion 102 and then extend beyond the wick 108 and/or the fill indicator element 110, as shown. In other embodiments, the support substrate 114 can support the entire carrier portion 102, at least a portion of the wick 108, and the entire fill indicator element 110 (not shown). In some embodiments, the support substrate 114 can be disposed under the carrier portion 102. In some embodiments, the support substrate 114 can be disposed along one or more sides of the carrier portion 102. In some embodiments, the support substrate 114 can be disposed under at least a portion of the carrier portion 102. In some embodiments, the support substrate 114 can be disposed under at least a portion of the wick 108. In other embodiments, the support substrate 114 can be disposed under at least a portion of the fill indicator element 110. It will be appreciated that the support substrate can form a physical barrier separating the test chemistry from the test subject.

Figure 7:
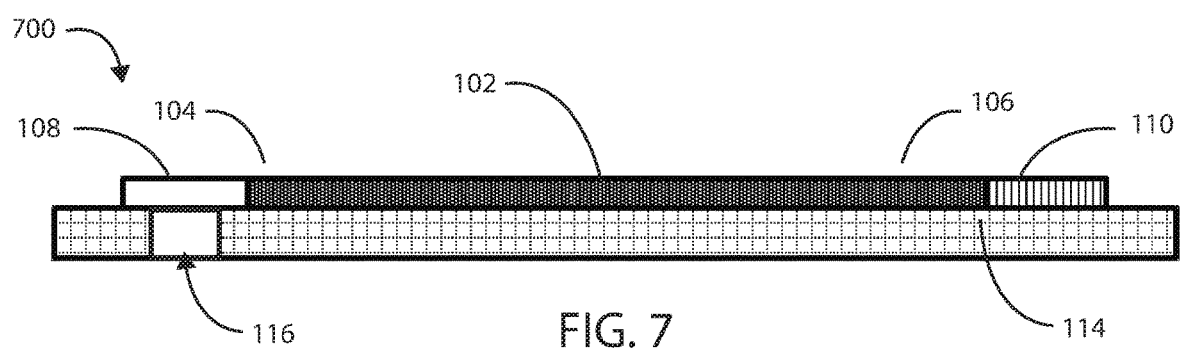
FIG. 7 is a schematic cross-sectional view of components of a testing article in accordance with various embodiments herein.

Referring now to FIG. 7, a cross-sectional view of a testing article 700 is shown in accordance to the embodiments herein. Similar to the testing article 500 shown in FIGS. 5 and 6, testing article 700 further includes a support substrate 114. The support substrate 114 of testing article 700 can include one or more support substrate openings 116 in the support substrate 114 to provide a physical access point for the fluid of the test subject to contact the wick 108. In some embodiments, the support substrate opening 116 is a void space with no material disposed therein. In other embodiments, the support substrate opening 116 can include a material that is the same material as wick 108. In yet other embodiments, the support substrate opening 116 can include an extension of one or more portions of wick 108.

Figure 8:
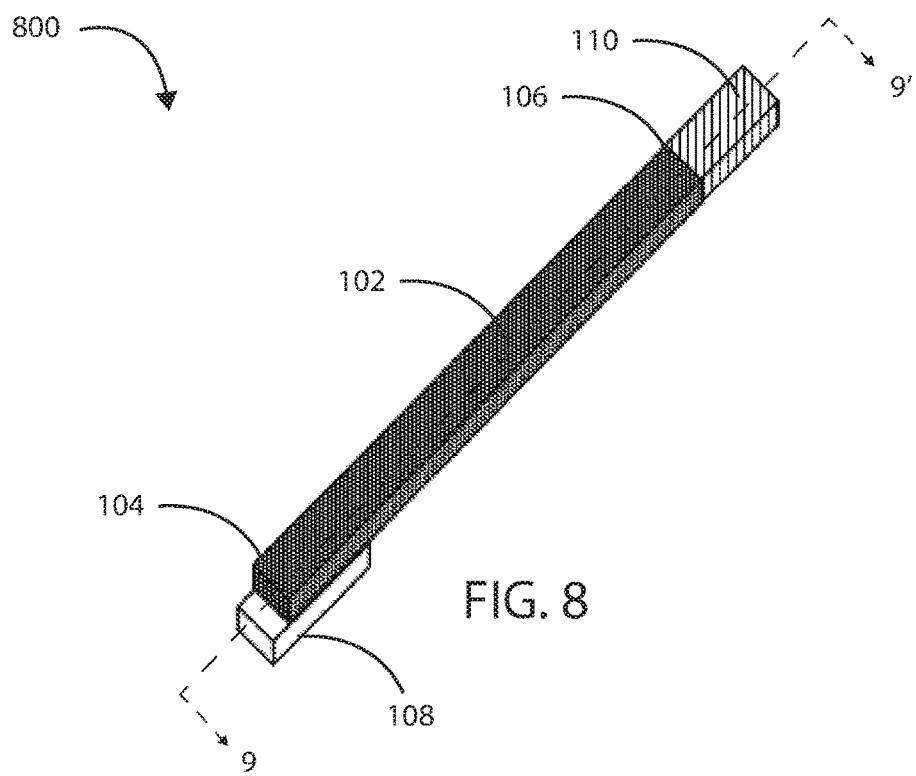
FIG. 8 is a schematic perspective view of components of a testing article in accordance with various embodiments herein.
Figure 9:
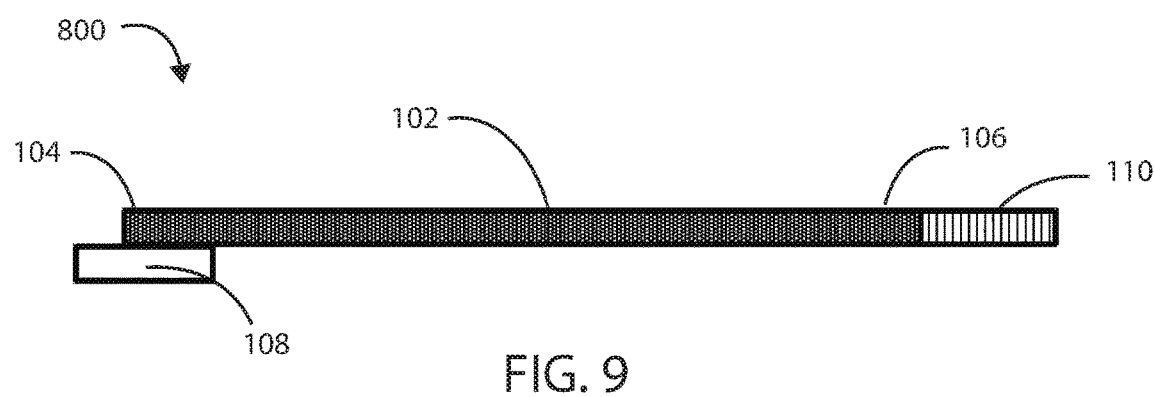
FIG. 9 is a schematic cross-sectional view of components of a testing article shown in FIG. 8 along line 9-9' in accordance with various embodiments herein.

The testing articles herein can include those that have a wick attached with an overlapping joint. Referring now to FIG. 8, a perspective view of a testing article 800 is shown in accordance with the embodiments herein. FIG. 9 shows a cross-sectional view of the testing article 800 of FIG. 8 along line 9-9'. The testing article 800 shown in FIGS. 8 and 9 can include a carrier portion 102, a wick 108, and/or a fill indicator element 110, in an array of configurations as described elsewhere herein. The wick 108 of testing article 800 is attached to the first end 104 of the carrier portion 102 via an overlapping joint. The degree of overlap to the joint between the wick and the absorbent layer can be tailored to control the ingress and uptake of the fluid of a test subject (e.g., sweat) to influence the timing and development of a hydration signal within the testing article.

The wick 108 as shown in FIGS. 8 and 9 can overlap with the carrier portion 102 (with either the wick or carrier portion on top—wherein the top is the side facing away from contact with the subject's skin and/or the side facing up with respect to gravity) such that at least 5% of the top surface area of wick 108 overlaps with the carrier portion 102. In some embodiments, the wick 108 can overlap with the carrier portion 102 such that at least 50% of the top surface area of wick 108 overlaps with the carrier portion 102. In other embodiments, the wick 108 can overlap with the carrier portion 102 such that at least 75% of the top surface area of wick 108 overlaps with the carrier portion 102. In some embodiments, the wick 108 can overlap with the carrier portion 102 such that 1%, 2%, 5%, 10%, 15%, 20%, 25%, 30%, 35%, 40%, 45%, 50%, 55%, 60%, 65%, 70%, 75%, 80%, 85%, 90%, 95%, or 100% of the top surface area of wick 108 overlaps with the carrier portion 102. It will be appreciated that the top surface area overlap between the wick 108 and bottom surface of the carrier portion 102 can fall within a range, wherein any of the forgoing overlap percentages can serve as the lower or upper bound of the range, provided that the lower bound of the range is a value less than the upper bound of the range. It will be appreciated that in some embodiments, the testing articles herein do not have a wick attached to the carrier portion with an overlapping joint, as discussed above in reference to FIGS. 1-7.

Figure 10:
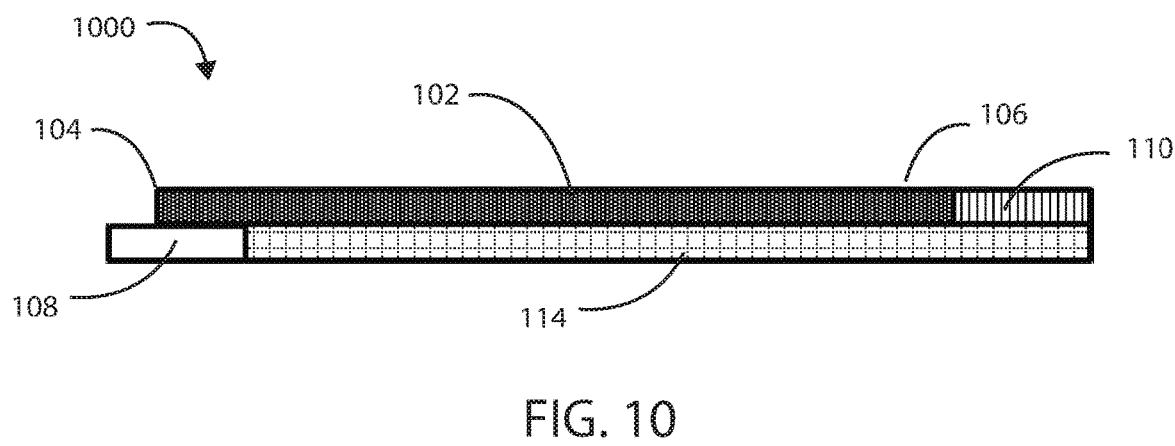
FIG. 10 is a schematic cross-sectional view of components of a testing article in accordance with various embodiments herein.

In embodiments where the wick is attached to the testing article with an overlapping joint, an additional support substrate can also be included. Referring now to FIG. 10, a cross-sectional view of a testing article 1000 is shown in accordance with the embodiments herein. Similar to the testing article 800 shown in FIG. 9, testing article 1000 further includes a support substrate 114. As discussed elsewhere herein, the support substrate 114 can provide structural support to the testing article along the carrier portion 102, the wick 108, and/or the fill indicator element 110. It will be appreciated that the support substrate 114 can also form a physical barrier separating the test chemistry from the test subject.

Figure 11:
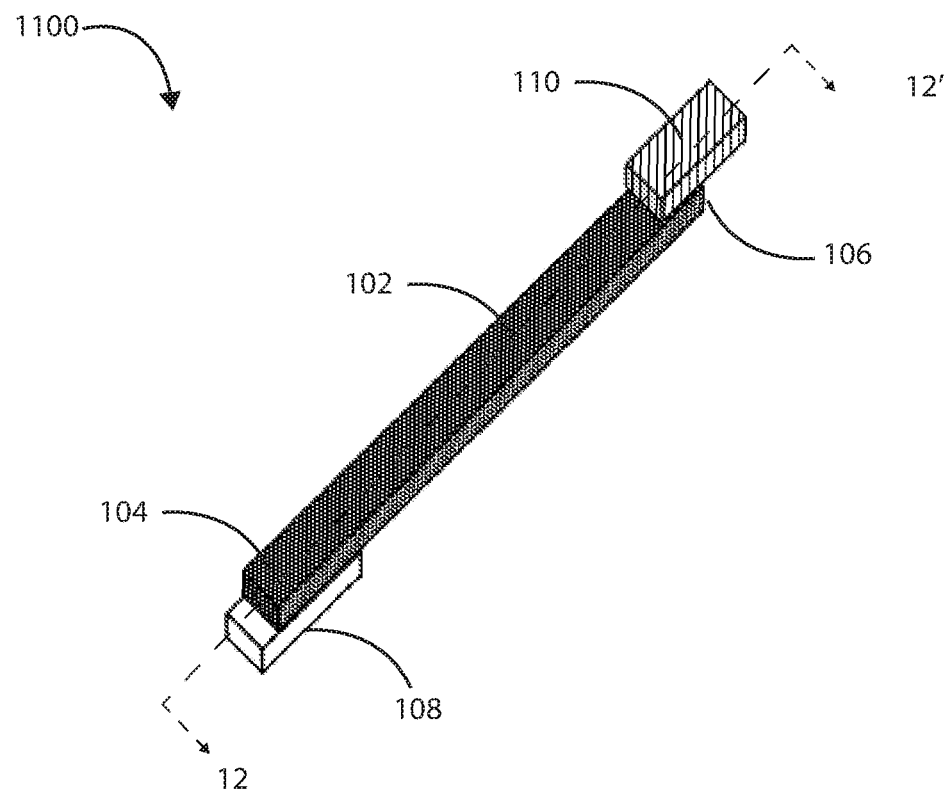
FIG. 11 is a schematic perspective view of components of a testing article in accordance with various embodiments herein.
Figure 12:
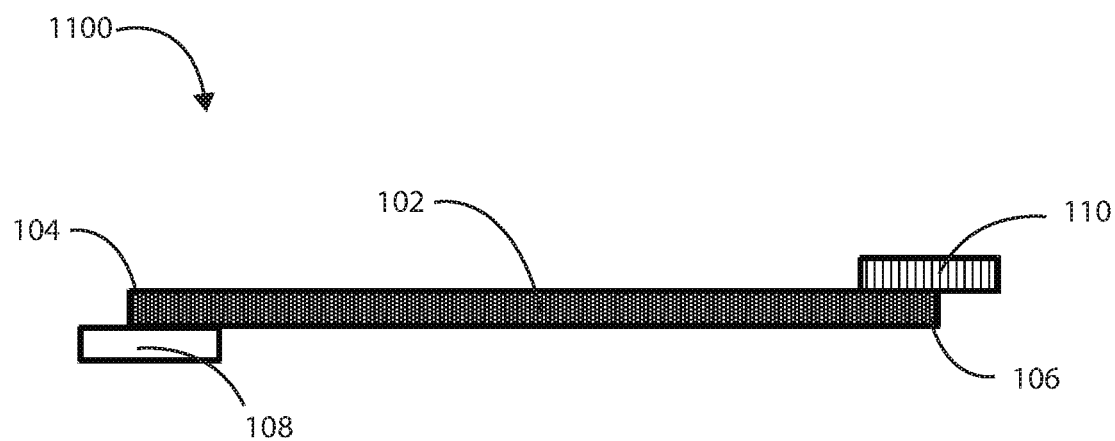
FIG. 12 is a schematic cross-sectional view of components of a testing article shown in FIG. 11 along line 12-12' in accordance with various embodiments herein.

The testing articles herein can include those that have a fill indicator element attached with an overlapping joint. Referring now to FIG. 11, a perspective view of a testing article 1100 is shown in accordance with the embodiments herein. FIG. 12 shows a cross-sectional view of the testing article 1100 of FIG. 11 along line 12-12'. The testing article 1100 shown in FIGS. 11 and 12 can include a carrier portion 102, a wick 108, and a fill indicator element 110, in an array of configurations as described elsewhere herein. The fill indicator element 110 of testing article 1100 is attached to the second end 106 of the carrier portion 102 via an overlapping joint. In embodiments where the fill indicator element is attached to the testing article with an overlapping joint, an additional support substrate can also be included (not shown). The degree of overlap to the joint between the absorbent layer and the fill indicator element can be tailored to control the ingress and uptake of the fluid of a test subject (e.g., sweat) to influence the timing and development of a hydration signal within the testing article.

The fill indicator element 110 as shown in FIGS. 11 and 12 can overlap with the carrier portion 102 such that at least 5% of the top surface area of fill indicator element 110 overlaps with the carrier portion 102. In some embodiments, the fill indicator element 110 can overlap with the carrier portion 102 such that at least 50% of the top surface area of fill indicator element 110 overlaps with the carrier portion 102. In other embodiments, the fill indicator element 110 can overlap with the carrier portion 102 such that at least 75% of the top surface area of fill indicator element 110 overlaps with the carrier portion 102. In some embodiments, the fill indicator element 110 can overlap with the carrier portion 102 such that 5%, 10%, 15%, 20%, 25%, 30%, 35%, 40%, 45%, 50%, 55%, 60%, 65%, 70%, 75%, 80%, 85%, 90%, 95%, or 100% of the top surface area of wick 108 overlaps with the bottom surface of the carrier portion 102. It will be appreciated that the top surface area overlap between the fill indicator element 110 and carrier portion 102 can fall within a range, wherein any of the forgoing overlap percentages can serve as the lower or upper bound of the range, provided that the lower bound of the range is a value less than the upper bound of the range. It will be appreciated that in some embodiments, the testing articles herein do not have a fill indicator element attached to the carrier portion with an overlapping joint, as discussed above in reference to FIGS. 1-7.

Figure 13:
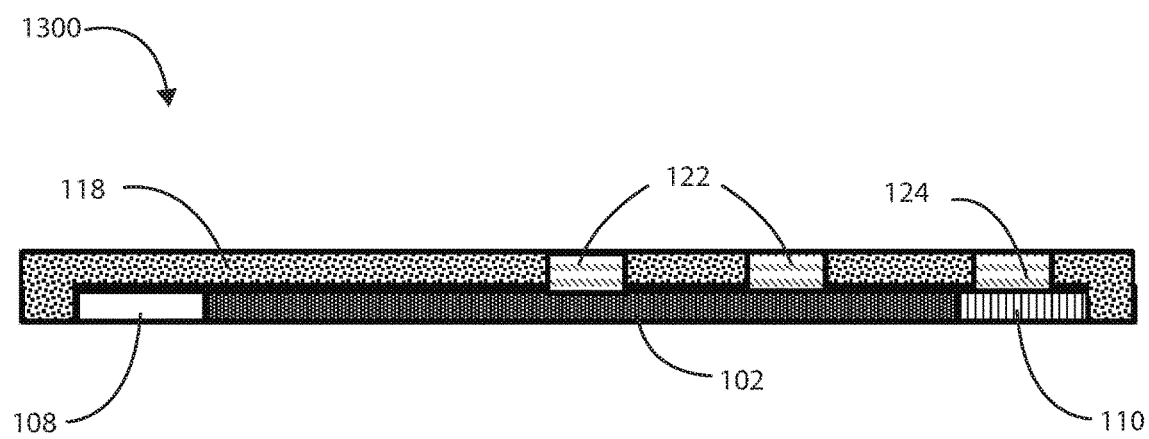
FIG. 13 is a schematic cross-sectional view of components of a testing article in accordance with various embodiments herein.
Figure 14:
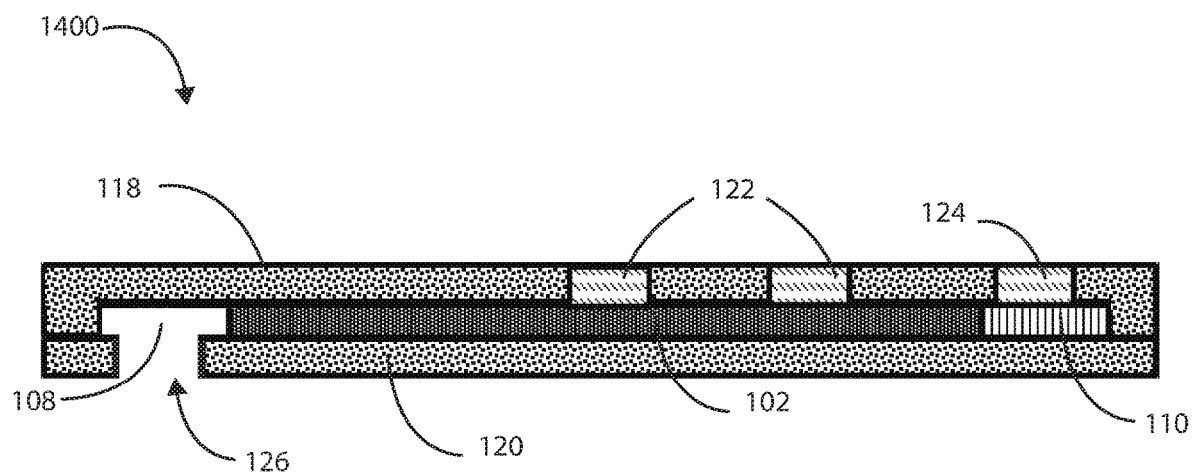
FIG. 14 is a schematic cross-sectional view of components of a testing article in accordance with various embodiments herein.

The testing articles described herein can also include one or more moisture vapor barrier layers, which in some embodiments can also serve as a support substrate. In some embodiments, the testing articles described herein can include a first moisture vapor barrier layer, a second moisture vapor barrier layer, or both. Referring now to FIGS. 13 and 14, cross-sectional views of testing article 1300 and testing article 1400, respectively, with various combinations of moisture barrier layers are shown in accordance with the embodiments herein. Testing article 1300 and testing article 1400 can include a carrier portion 102, a wick 108, and/or a fill indicator element 110, in an array of configurations as described elsewhere herein. In some embodiments, the moisture vapor barriers described herein can be formed from a polymer, such as a sufficiently water impermeable polymer. Testing articles that have a first or second moisture barrier layer can further include a support substrate, as described elsewhere herein. It will be appreciated that the moisture barriers described herein (as well as other components) can include various indicia, including, but not limited to logos, instructions for use, figures, hydration indicators, and the like, which can be placed on various surfaces of the components including the top, bottom, etc.

Testing article 1300 includes a first moisture vapor barrier layer 118 disposed over the carrier portion 102. When the testing article 1300 is affixed to the skin of a subject the first moisture vapor barrier layer 118 can act to encapsulate the carrier portion 102, the wick 108, and/or the fill indicator element 110, to prevent the influx of environmental fluids not specific to the test subject. To observe a first color change in the carrier portion 102 of the testing article 1300, at least one carrier portion optical window 122 can be disposed within the first moisture vapor barrier layer 118 directly above the carrier portion 102. To observe a second color change in the fill indicator element 110, an additional fill indicator element optical window 124 can be disposed within the first moisture vapor barrier layer 118 directly above the fill indicator element 110.

In some embodiments the first moisture vapor barrier layer 118 can be opaque. In other embodiments the first moisture vapor barrier layer 118 can be transparent. The optical access window(s) 122 and the fill indicator element optical window 124 can be transparent or can be formed of another material that is different than the vapor barrier layer 118. In some embodiments, optical access window(s) 122 and the fill indicator element optical window 124 are made from the same material as the vapor barrier layer 118, which can be a transparent material and there is an ink layer (or other printing) over portions of the vapor barrier layer 118 rendering it opaque, but not over the optical access window (s) 122 and the fill indicator element optical window 124 allowing them to remain transparent.

In some embodiments, optical access windows can include a hydrochromic ink that turns from opaque to clear in the presence of water. As such, the hydrochromic ink can visually obscure the optical access window until water (such as provided by the fluid from the test subject) contacts the hydrochromic ink and causes it to become clear allowing a user or device to see through the optical access window. For example, in some embodiments, the optical access window (s) 122 and the fill indicator element optical window 124 are made from a transparent material and an opaque hydrochromic ink is applied thereto. When the ink comes into contact with moisture (i.e. the sweat sample), it becomes transparent, revealing the leading edge of the color change.

In some embodiments the first moisture vapor barrier layer 118 can be waterproof. In other embodiments the first moisture vapor barrier layer 118 can be water resistant. It will be appreciated that both the carrier portion optical window 122 and the fill indicator element optical window 124 can be transparent to provide easy viewing access to the components within. However, in some embodiments optical access window(s) 122 can be omitted.

The presence of a first moisture vapor barrier layer 118 disposed over the components of the testing article 1300 can improve or enhance the collection of sweat from users with low sweat rates (e.g., <1 g/m$^2$/min—See "CLSI C34-A3 Sweat Testing: Sample Collection and Quantitative Chloride Analysis" Approved Guideline—3$^{rd}$ Edition), such as the elderly or the ill, by stimulating sweating within the local environment of the testing article.

Testing article 1400 includes a first moisture vapor barrier layer 118 disposed over the carrier portion 102 and a second moisture vapor barrier layer 120 disposed under the carrier portion 102. When the first moisture vapor barrier layer 118 and the second moisture vapor barrier layer 120 are combined, together they can encapsulate the carrier portion 102, a portion of the wick 108, and/or the fill indicator element 110 to prevent the influx of environmental fluids not specific to the test subject. The first moisture vapor barrier layer 118 and the second moisture vapor barrier layer 120 can be laminated over and around the carrier portion 102, a portion of the wick 108, and/or the fill indicator element 110. In some embodiments, the first moisture vapor barrier layer 118 and the second moisture vapor barrier layer 120 can be deposited over and around the carrier portion 102, a portion of the wick 108, and/or the fill indicator element 110 and sealed together. In some embodiments the second moisture vapor barrier layer 120 can be opaque. In other embodiments the second moisture vapor barrier layer 120 can be transparent. In some embodiments the second moisture vapor barrier layer 120 can be waterproof. In other embodiments the second moisture vapor barrier layer 120 can be water resistant.

In embodiments where the first moisture vapor barrier layer 118 and the second moisture vapor barrier layer 120 encapsulate the carrier portion 102, a portion of the wick 108, and/or fill indicator element 110, such as in testing article 1400 shown in FIG. 14, at least one wick opening 126 in the second moisture vapor barrier layer 120 is included to provide a physical access point for the fluid of the subject to contact the wick 108. To observe a first color change in the carrier portion 102 of the testing article 1400, at least one carrier portion optical window 122 can be disposed within the moisture vapor barrier layer 118 directly above the carrier portion 102. To observe a second color change in the fill indicator element 110, an additional fill indicator element optical window 124 can be disposed within the moisture vapor barrier layer 118 directly above the fill indicator element 110.

When the first moisture vapor barrier layer 118 and/or the second moisture vapor barrier layer 120 encapsulate a portion of the wick 108, it will be appreciated that the majority of the surface area of the wick 108 will be accessible to the fluid of a test subject through at least one physical opening in the first moisture vapor barrier layer 118 and/or the second moisture vapor barrier layer 120. In some embodiments, the surface area of the wick 108 accessible to the fluid of a test subject through at least one physical opening in a first moisture barrier layer and/or a second moisture barrier layer is a least 95% of the surface area of the wick 108. In some embodiments, the surface area of the wick 108 accessible to the fluid of a test subject through at least one physical opening in a first moisture barrier layer and/or a second moisture barrier layer is a least 75% of the surface area of the wick 108.

In some embodiments, the exposed surface area of the wick 108 as shown in FIGS. 13 and 14 is accessible to the fluid of a test subject through at least one physical opening in a first moisture barrier layer and/or a second moisture barrier layer is a least 5%, 10%, 15%, 20%, 25%, 30%, 35%, 40%, 45%, 50%, 55%, 60%, 65%, 70%, 75%, 80%, 85%, 90%, 95%, or 100% of the surface area of wick 108. It will be appreciated that the exposed surface area of the wick 108 accessible to the fluid of a test subject through at least one physical opening in a first moisture barrier layer and/or a second moisture barrier layer can fall within a range, wherein any of the forgoing overlap percentages can serve as the lower or upper bound of the range, provided that the lower bound of the range is a value less than the upper bound of the range.

The testing articles described herein can further include an adhesive layer disposed over any combination of the components, including a carrier portion 102, a wick 108, a fill indicator element 110, a support substrate 114, a first moisture vapor barrier layer 118, and/or a second moisture vapor barrier layer 120, to adhere the testing article to the skin of a test subject. In some embodiments, when adhesive layer is disposed over the components, it can be made from water impermeable materials. In some embodiments, the adhesive layer can be made of water permeable materials and can be disposed under the components of the testing article.

Figure 15:
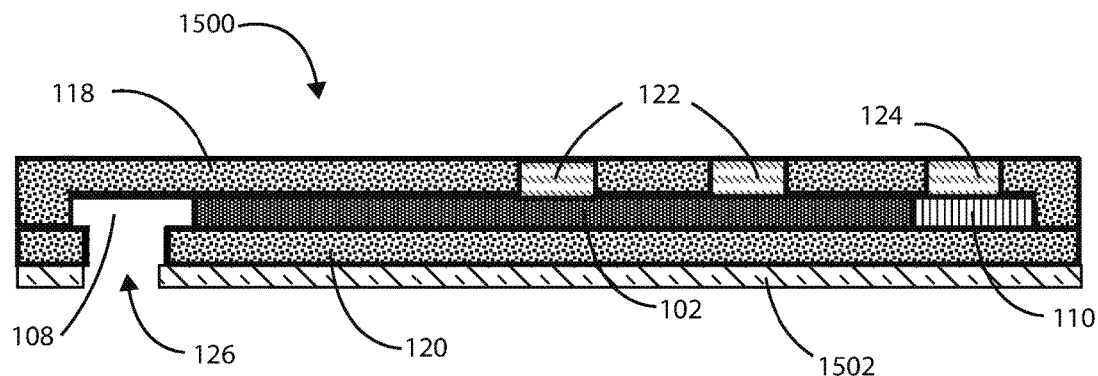
FIG. 15 is a schematic cross-sectional view of components of a testing article in accordance with various embodiments herein.

Referring now to FIG. 15, a schematic cross-sectional view is shown of components of a testing article 1500 in accordance with various embodiments herein. The elements in FIG. 15 are substantially the same as shown in FIG. 14. However, FIG. 15 also shows an adhesive layer 1502. The adhesive layer 1502 can be useful for adhering the testing article to the skin of a test subject. Many different materials can be used to form the adhesive layer 1502 including, but not limited to, adhesives used for adhesive bandages such as a tacky pressure sensitive adhesive such as acrylic, polyolefin, polyurethane, rubber, and silicone-based adhesives, in some cases including tackifier resins.

Figure 16:
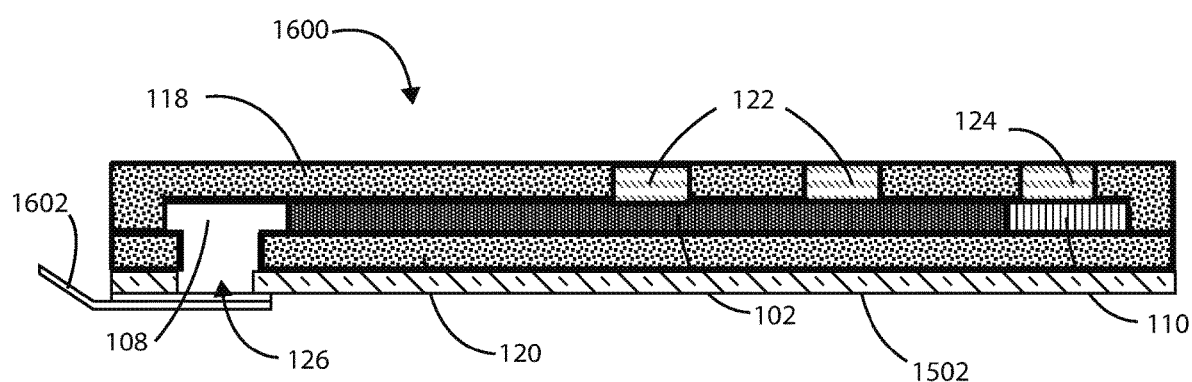
FIG. 16 is a schematic cross-sectional view of components of a testing article in accordance with various embodiments herein.

In some embodiments, it may be convenient to adhere the testing article to the skin of a test subject at a first time point (such as before a workout begins), but not allow sweat to enter through the wick until a later time point so that the degree of hydration revealed through the use of the testing article reflects hydration at a later time point (such as midway through a workout, just after a workout ended, etc.). This delayed action of the testing article can be accommodated in various ways. In a particular embodiment, an activation tab can be disposed under the wick and then removed to expose the wick at a later time point (e.g., a time point later than when the testing article is first adhered to a test subject's skin). Referring now to FIG. 16 is a schematic cross-sectional view of components of a testing article 1600 in accordance with various embodiments herein. The elements in FIG. 15 are substantially the same as shown in FIG. 14. However, FIG. 16 also shows an activation tab 1602 (or release liner) sealing off the wick 108. The activation tab 1602 can be formed of a material that does not allow the passage of moisture there through. In various embodiments, the activation tab 1602 can be formed of a water impermeable polymer. When a user wants to activate the testing article, they can simply pull on the end of the activation tab 1602 causing it to release and expose the wick 108.

Figure 17:
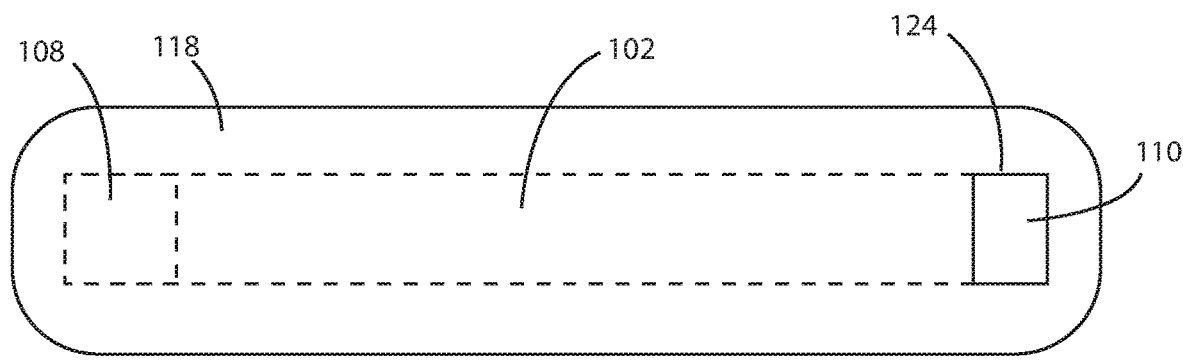
FIG. 17 is a schematic top plan view of a testing article in accordance with various embodiments herein.

Referring now to FIG. 17, a schematic top plan view of a testing article is shown in accordance with various embodiments herein. In this view, the moisture vapor barrier layer 118 of the testing article can be seen along with the fill indicator element 110. In this example, the moisture vapor barrier layer 118 is opaque and thus the carrier portion 102 and the wick 108 are not directly viewable. Further, in this embodiment, the results of the hydration test cannot be viewed from the top of the device. Rather, the testing article must be removed from the skin and flipped over to assess the degree of hydration from the bottom. Removing the testing article from the skin and flipping it over to view the results can be triggered by the wearer (or a third party) observing that the fill indicator element 110 has changed colors. It will be appreciated that in some embodiments, the testing article can be analyzed from the top of the testing article while affixed to a test subject, while in other embodiments the testing article can be analyzed from the bottom of the testing article after removal from the test subject.

Figure 18:
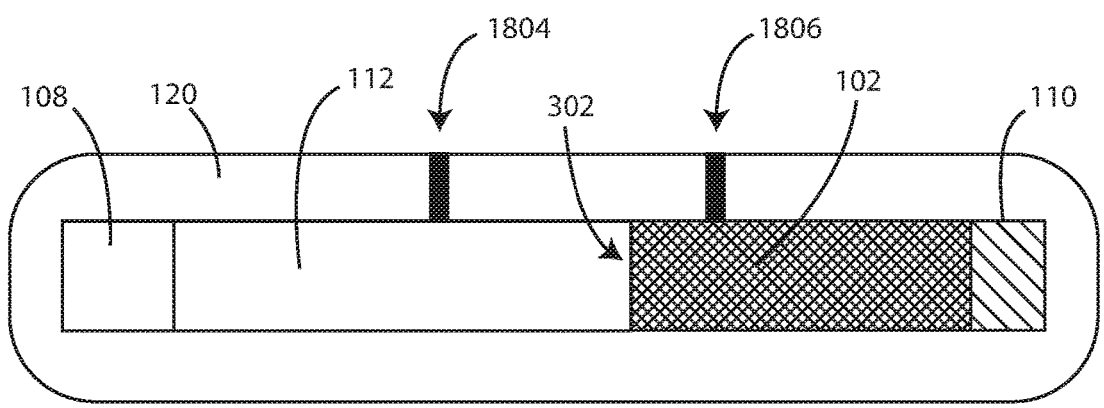
FIG. 18 is a schematic bottom plan view of a testing article in accordance with various embodiments herein.

Referring now to FIG. 18, a schematic bottom plan view of a testing article is shown in accordance with various embodiments herein. The underside of the moisture vapor barrier layer 120 and/or adhesive layer can include testing assessment lines 1804 and 1806. The first color change 112 (resulting from reaction with chloride ions) includes a leading edge 302. The testing article user can compare the position of the leading edge with the position of the testing assessment lines 1804 and 1806. In this example, if the leading edge 302 is between the wick 108 and testing assessment line 1804, then the individual can be deemed to be adequately hydrated. If the leading edge 302, is between testing assessment line 1804 and testing assessment line 1806, then the individual can be deemed to be mildly to moderately dehydrated. If the leading edge 302 is between the testing assessment line 1806 and the fill indicator element 110, then the individual can be deemed to be severely dehydrated. While two testing assessment lines and three categories of hydration are illustrated in this example, it will be appreciated that embodiments herein can include from 1 to 20 or more testing assessment lines and from 2 to 21 or more categories of hydration.

It will be appreciated that a dual testing article is contemplated herein. By way of example, referring now to FIG. 19, a schematic top plan view of a dual testing article 1900 is shown in accordance with various embodiments herein. In this view, the dual testing article 1900 can include a moisture vapor barrier layer 118 as seen along with two fill indicator elements 110. In this example, the moisture vapor barrier layer 118 is opaque and thus the carrier portions 102 and the wicks 108 are not directly viewable. Further, in this embodiment, the results of the hydration test cannot be viewed from the top of the device. Rather, the dual testing article 1900 must be removed from the skin and flipped over to assess the degree of hydration from the bottom. Removing the dual testing article 1900 from the skin and flipping it over to view the results can be triggered by the wearer (or a third party) observing that the fill indicator element(s) 110 have changed colors.

Figure 20:
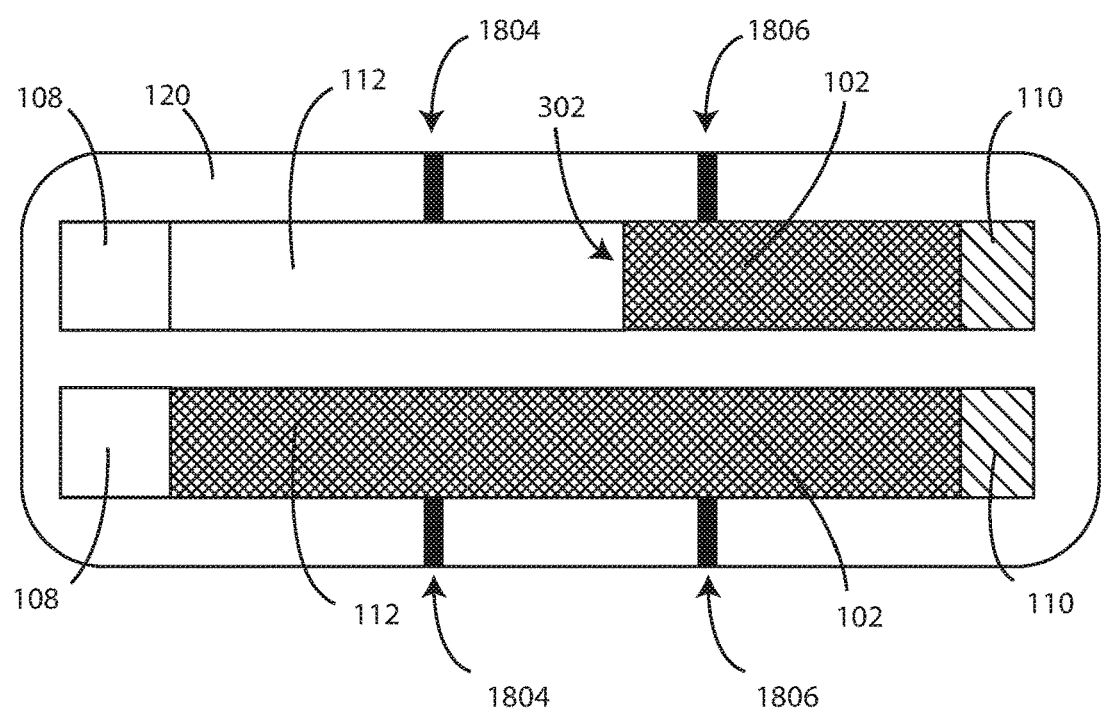
FIG. 20 is a schematic bottom plan view of a testing article in accordance with various embodiments herein.

Referring now to FIG. 20, a schematic bottom plan view of a dual testing article 1900 is shown in accordance with various embodiments herein. The underside of the moisture vapor barrier layer 120 and/or adhesive layer can include testing assessment lines 1804 and 1806 on either side of the carrier portions 102. The first color change 112 (resulting from reaction with chloride ions) includes a leading edge 302. The dual testing article user can compare the position of the leading edge with the position of the testing assessment lines 1804 and 1806, as discussed above in reference to FIG. 17. The dual testing article 1900 shown in FIG. 20 reveals one activated carrier portion 102 having a leading edge 302 disposed between testing assessment lines 1804 and 1806, while the other carrier portion 102 remains inactive.

Figure 19:
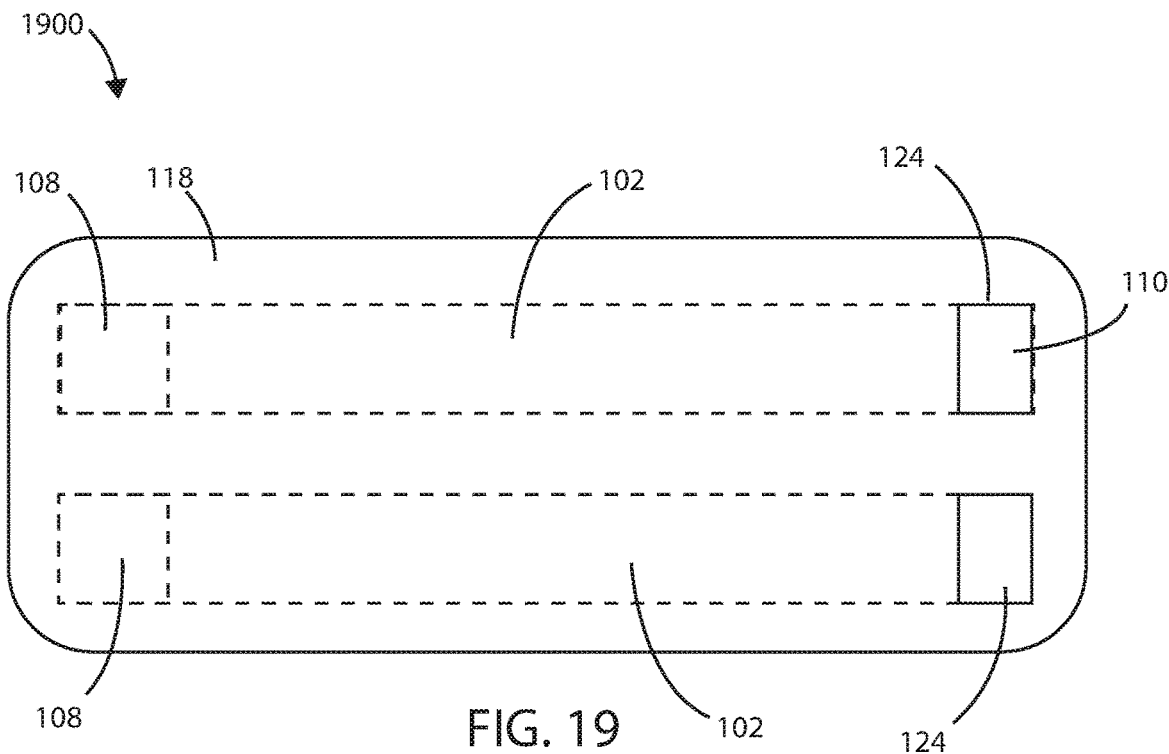
FIG. 19 is a schematic top plan view of a testing article in accordance with various embodiments herein.

The dual testing article 1900 shown in FIGS. 19 and 20 can include an activation tab (not shown) on either or both of the wicks 108, such that the user can activate one of the testing articles at a desired time point and can activate the other testing article at a different time point. In some embodiments, the dual testing article can be used to determine a baseline hydration state of a test subject and then a hydration state of the test subject at some time after the initiation of an athletic endeavor, physical labor, or the like. While the embodiments shown in FIGS. 19 and 20 show a dual testing article, it will be appreciated that the testing articles herein can include more than two testing articles in many configurations.

Testing Article Shapes

The testing articles described herein can assume various shapes and sizes. The testing articles herein can include two lateral edges, where the two lateral edges can define the shape of the testing article. For example, the embodiments shown in FIGS. 1-20 include an elongate linear strip shape where the cross-sectional area of the carrier portion is substantially constant along its length between its first end and the second end, and the two lateral edges remain parallel. In other embodiments, the cross-sectional area of the carrier portion can vary along its length between the first end and the second end. For example, in some embodiments, the average cross-sectional area of the carrier portion at its first end can be greater than at its second end. In other embodiments, the average cross-sectional area of the carrier portion at its second end can be greater than at its first end.

Figure 21:
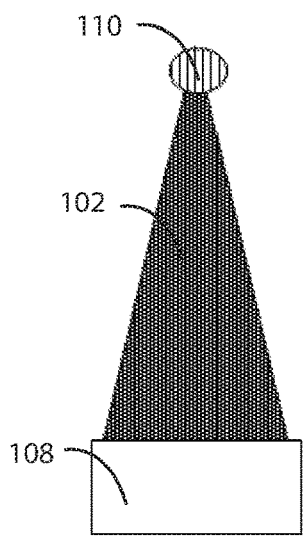
FIG. 21 is a schematic top-down view of components of a testing article in accordance with various embodiments herein.
Figure 22:
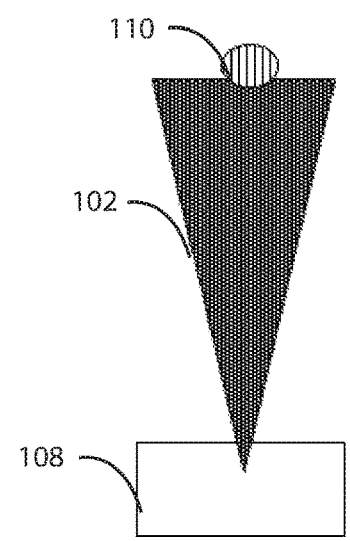
FIG. 22 is a schematic top-down view of components of a testing article in accordance with various embodiments herein.

Referring now to FIGS. 21-26, top-down views of a variety of testing articles are shown in accordance with the embodiments herein. In FIGS. 21 and 22, each testing article is shown with a carrier portion having a triangular shape. In FIG. 21, the average cross-sectional area of the carrier portion at the first end is greater than at the second end, while in FIG. 22, the average cross-sectional area of the carrier portion at the second end is greater than at the first end. It will be appreciated that the triangular shape can be tailored to control and influence the shape of the boundary between the reacted portion of the carrier portion 102 and the unreacted portion of the carrier portion 102. Tailoring the shape by altering the angles of the triangle can provide a straight reaction front between the reacted and unreacted portions of the carrier portion 102 as the fluid flows through it.

Figure 23:
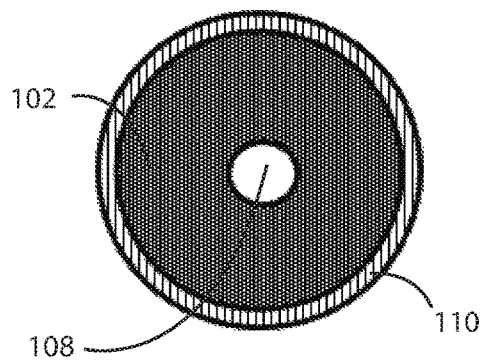
FIG. 23 is a schematic top-down view of components of a testing article in accordance with various embodiments herein.
Figure 24:
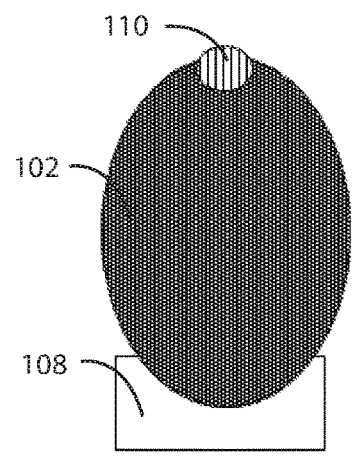
FIG. 24 is a schematic top-down view of components of a testing article in accordance with various embodiments herein.

The testing article shown in FIG. 23 includes a testing article having a circular shape. FIG. 24 shows the wick 108 disposed in the center of the testing article, a carrier portion 102 disposed circumferentially about the wick 108, and a fill indicator element 110 disposed circumferentially about the carrier portion 102. The testing article shown in FIG. 24 has an ovoid shape.

Figure 25:
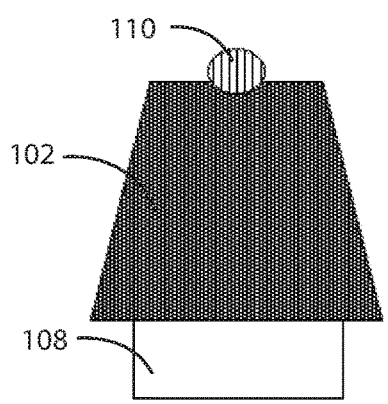
FIG. 25 is a schematic top-down view of components of a testing article in accordance with various embodiments herein.
Figure 26:
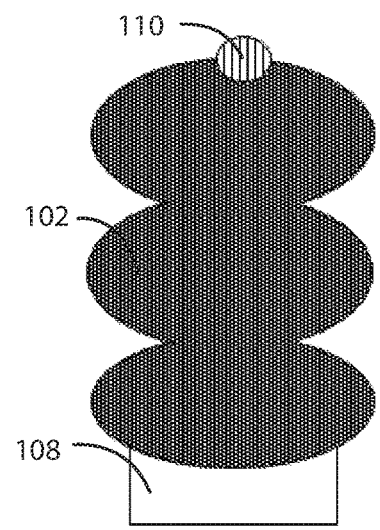
FIG. 26 is a schematic top-down view of components of a testing article in accordance with various embodiments herein.

The testing article shown in FIG. 25 has a trapezoidal shape and the testing article shown in FIG. 26 includes one having a carrier portion with two lateral edges, where the lateral edges define a scalloped shape. The trapezoidal shape of FIG. 25 and the scalloped shape of FIG. 26 can be tailored to control the flow of fluid through the carrier portion. Impedance to the flow of fluid through the carrier portion is based on the cross-sectional area of the carrier portion, and as such, the cross-sectional area can be manipulated to either increase or decrease the flow rate of the fluid.

As discussed elsewhere herein, the testing articles can further include any combination of components, including an adhesive layer (not shown), a carrier portion 102, a wick 108, a fill indicator element 110, a support substrate 114, a first moisture vapor barrier layer 118, and/or a second moisture vapor barrier layer 120. It will be appreciated that the shape of each component can include (in entirety or portions thereof) that are circular, rectangular, square, oval (or ovoid), triangular, trapezoidal, polygonal, curvilinear, straight, irregular, and the like.

Folded Configurations

Figure 27:
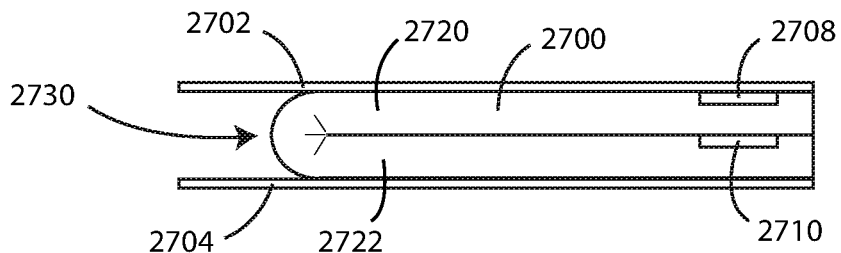
FIG. 27 is a schematic side view of a testing article in accordance with various embodiments herein.

In some embodiments, the testing article can be folded over on itself in order to prevent the ingress of a fluid into the testing article until a desired time. Referring now to FIG. 27 a schematic side view is shown of a testing article in accordance with various embodiments herein. The testing article 2700 includes a fold 2730 (or curved portion) such that the testing article is overlapped on itself such that there is an upper portion 2720 and a lower portion 2722. For ease of illustration, certain detailed aspects of the construction of the testing article 2700 are omitted from FIGS. 27-29 but can be as described previously for other figures. In this view, a first release-liner 2702 is disposed a first side of the testing article 2700 and a second release-liner 2704 is disposed on an opposite side of the testing article 2700. The first release-liner 2702 can cover a portion of the testing article 2700 including a wick 2708 (or aperture or proximal segment of a carrier portion in wickless embodiments) and an adhesive layer (not shown in this view). The second release-liner 2704 can cover a different portion of the testing article 2700 including, for example, an adhesive layer (not shown in this view). In some embodiments, a fill indicator (element and/or window) 2710 can be disposed on an upper surface of the lower portion 2722.

Figure 28:
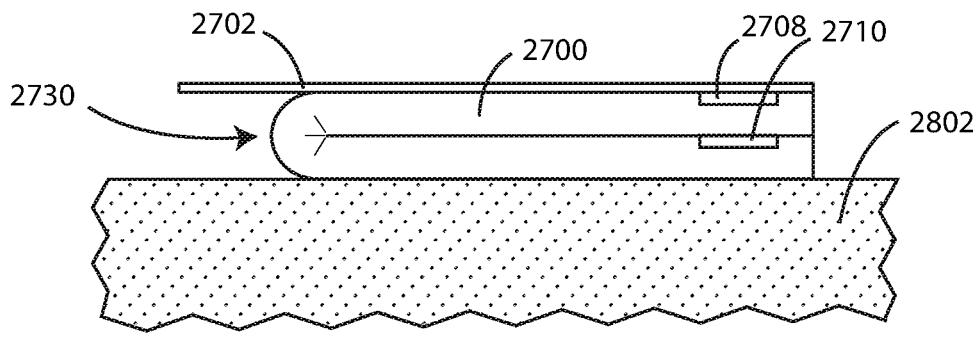
FIG. 28 is a schematic side view of a testing article in accordance with various embodiments herein as mounted on the skin of a subject in a first configuration.

As a first step of use, the second release-liner 2704 can be removed and the testing article 2700 can be placed on the skin 2802 of a test subject. Referring now to FIG. 28, a schematic side view is shown of a testing article 2700 in accordance with various embodiments herein as mounted on the skin 2802 of a subject in a first configuration. At this point, because the wick 2708 is not in contact with the skin 2802 and covered by the first release-liner 2702, a fluid of the test subject cannot enter the wick 2708 and thus the start of the test can be delayed for a period of time after the testing article 2700 is placed on the skin 2802.

Figure 29:
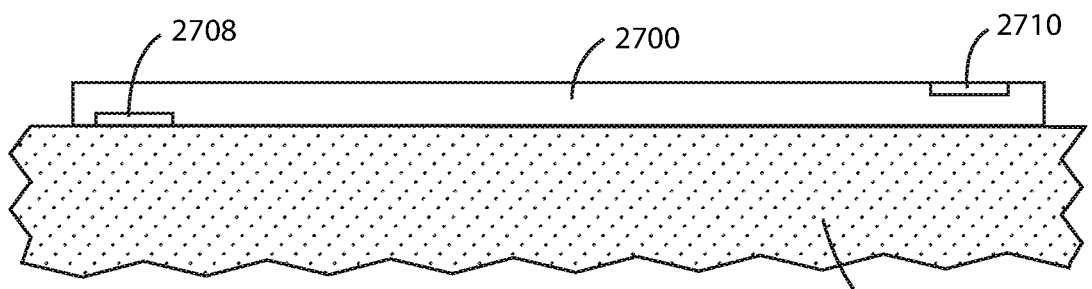
FIG. 29 is a schematic side view of a testing article in accordance with various embodiments herein as mounted on the skin of a subject in a first configuration.

As a second step of use, the first release-liner 2702 can be removed and the testing article 2700 can be straightened such that the upper portion 2720 is also brought into contact with the skin 2802 of the subject. Referring now to FIG. 29, a schematic side view is shown of a testing article 2700 in accordance with various embodiments herein as mounted on the skin 2802 of a subject in a first configuration. When the wick 2708 is put into contact with the skin 2802, then fluid from the test subject can begin to enter the testing article 2700 allowing the testing of fluids to begin. In some embodiments, such as when fill indicator 2710 indicates that a sufficient amount of fluids have entered the testing article 2700, the upper portion 2720 can be lifted off of the skin 2802 to stop the testing process.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A testing article to assess hydration of a test subject, the testing article comprising:

a carrier portion comprising a porous medium through which a fluid of the test subject moves, the carrier portion comprising a first end and a second end opposite the first end, wherein the fluid of the test subject enters the carrier portion at or near the first end;

a first chemical composition disposed in the porous medium, wherein the chemical composition reacts with chloride ions to produce a first color change;

a wick, wherein the wick is in direct contact with the first end of the carrier portion to allow the transfer of the fluid from the wick to the carrier portion;

a fill indicator element in direct contact with the second end of the carrier portion to allow the transfer of the fluid from the carrier portion to the fill indicator element; and a second chemical composition that reacts with the fluid of the test subject to produce a second color change, wherein the second color change is different than the first color change, wherein the second chemical composition is disposed in the porous medium of the carrier portion; wherein the second chemical composition is configured to migrate along with the fluid of the test subject through the porous medium of the carrier portion and into the fill indicator element.

2. The testing article of claim 1, wherein the wick lacks the first chemical composition.

3. The testing article of claim 1, wherein the wick is attached to the carrier portion by virtue of a joint selected from the group consisting of a butt joint or an overlapping joint.

4. The testing article of claim 1, the wick comprising a porous medium, wherein the porous medium of the wick exhibits greater wicking efficiency than the porous medium of the carrier portion.

5. The testing article of claim 1, further comprising an activation tab disposed under the wick, the activation tab configured to be removed to expose a portion the wick at a later time point.

6. The testing article of claim 1, the first chemical composition comprising silver chromate.

7. The testing article of claim 1, the second chemical composition comprising at least one of phenol red, methyl orange, brilliant yellow, bromocresol green, malachite green, bromophenol blue, or bromocresol purple.

8. The testing article of claim 1, wherein the cross-sectional area of the carrier portion varies along its length between the first end and the second end.

9. The testing article of claim 1, the carrier portion comprising two lateral edges, the lateral edges defining a scalloped shape.

10. The testing article of claim 1, further comprising a moisture vapor barrier layer; wherein the moisture vapor barrier layer encapsulates at least one of the carrier portion, the fill indicator element, or a portion of the wick.

11. The testing article of claim 1, further comprising a first moisture vapor barrier layer disposed on a first side of the carrier portion and a second moisture vapor barrier layer disposed on a second side of the carrier portion, wherein the second side of the carrier portion is opposite the first side of the carrier portion.

12. The testing article of claim 11, wherein the first moisture vapor barrier layer is opaque.

13. The testing article of claim 11, wherein the first moisture vapor barrier layer defines one or more transparent windows.

14. The testing article of claim 13, further comprising an opaque hydrochromic ink optically obscuring at least one of the transparent windows.

15. The testing article of claim 1, the first chemical composition further comprising a buffer having a pH of between 5.46 and 7.5.

16. The testing article of claim 1, wherein the carrier portion includes a curved portion dividing an upper portion of the carrier portion and a lower portion of the carrier portion, wherein the upper portion of the carrier portion is disposed on top of the lower portion of the carrier portion; further comprising a first release-liner disposed over a top surface of the upper portion of the carrier portion and a second release-liner disposed under a lower surface of the lower portion of the carrier portion.

17. A testing article to assess hydration of a test subject, the testing article comprising:

a carrier portion comprising a porous medium through which a fluid of the test subject moves, the carrier portion comprising a first end and a second end opposite the first end, wherein the fluid of the test subject enters the carrier portion at or near the first end;

a first chemical composition disposed in the porous medium, wherein the chemical composition reacts with chloride ions to produce a first color change, and wherein the chemical composition comprises a buffer having a pH of between 5.46 and 7.5; and a wick, wherein the wick is in direct contact with the first end of the carrier portion to allow the transfer of the fluid from the wick to the carrier portion.

18. The testing article of claim 17, further comprising a fill indicator element in direct contact with the second end of the carrier portion to allow the transfer of fluid from the carrier portion to the fill indicator element.

19. The testing article of claim 18, an absorbent layer comprising a second chemical composition that reacts with the fluid of the test subject to produce a second color change, wherein the second color change is different than the first color change.

20. The testing article of claim 18, the fill indicator element comprising a second chemical composition that reacts with the fluid of the test subject to produce a second color change, wherein the second color change is different than the first color change.

21. A testing article to assess hydration of a test subject, the testing article comprising:

a carrier portion comprising a porous medium through which a fluid of the test subject moves, the carrier portion comprising a first end and a second end opposite the first end, wherein the fluid of the test subject enters the carrier portion at or near the first end;

a first chemical composition disposed in the porous medium, wherein the chemical composition reacts with chloride ions to produce a first color change; and a fill indicator element in direct contact with the second end of the carrier portion to allow the transfer of the fluid from the carrier portion to the fill indicator element;

further comprising a moisture vapor barrier layer and an aperture in the moisture vapor barrier layer through which the fluid of the test subject passes before contacting the carrier portion; and wherein the carrier portion includes a curved portion dividing an upper portion of the carrier portion and a lower portion of the carrier portion, wherein the upper portion of the carrier portion is disposed on top of the lower portion of the carrier portion; further comprising a first release-liner disposed over a top surface of the upper portion of the carrier portion and a second release-liner disposed under a lower surface of the lower portion of the carrier portion.

\* \* \* \* \*